(12) United States Patent
Kordes et al.

(10) Patent No.: US 7,871,960 B2
(45) Date of Patent: Jan. 18, 2011

(54) 1-(IMIDAZOLIN-2-YL)AMINO-1,2-DIPHENYLETHANE COMPOUNDS FOR COMBATING ANIMAL PESTS

(75) Inventors: Markus Kordes, Frankenthal (DE); Norbert Götz, Worms (DE); Michael Rack, Eppelheim (DE); Christopher Koradin, Ludwigshafen (DE); Livio Tedeschi, Mannheim (DE); Deborah L. Culbertson, Fuquay-Varina, NC (US)

(73) Assignee: BASF SE, Ludwigshafen (DE)

( * ) Notice: Subject to any disclaimer, the term of this patent is extended or adjusted under 35 U.S.C. 154(b) by 352 days.

(21) Appl. No.: 11/914,992

(22) PCT Filed: May 18, 2006

(86) PCT No.: PCT/EP2006/062419
§ 371 (c)(1),
(2), (4) Date: Nov. 20, 2007

(87) PCT Pub. No.: WO2006/125748
PCT Pub. Date: Nov. 30, 2006

(65) Prior Publication Data
US 2008/0200335 A1    Aug. 21, 2008

Related U.S. Application Data

(60) Provisional application No. 60/684,122, filed on May 24, 2005, provisional application No. 60/736,714, filed on Nov. 15, 2005.

(51) Int. Cl.
*A01N 43/50* (2006.01)
*C07D 233/04* (2006.01)

(52) U.S. Cl. .................. 504/275; 548/326.5; 548/331.5; 504/261

(58) Field of Classification Search .............. 548/300.1, 548/326.5, 331.5; 514/385, 396, 398; 504/261, 504/275
See application file for complete search history.

(56) References Cited

U.S. PATENT DOCUMENTS 7,655,600 B2 *   2/2010   Kordes et al. ............... 504/266

FOREIGN PATENT DOCUMENTS

| | | |
|---|---|---|
| DE | 39 08 814 | 9/1990 |
| EP | 0 058 635 | 8/1982 |
| GB | 2092582 | 8/1982 |
| WO | WO 2005/063724 | 7/2005 |

OTHER PUBLICATIONS

International Preliminary Report on Patentability and Written Opinion of the International Searching Authority for International Application No. PCT/EP2006/062419.
DW 90-283917/38, Bayer AG, 16.01.90-DE-000972 (+DE-908814) (Sep. 19, 1990) Insecticide compsns. For controlling textile pests—contg. Nitro-methylene- or nitro-imino imidazolidine derives. 1990 Derwent Publications Ltd., Eng. Equivalent to DE 39 08 814.

* cited by examiner

*Primary Examiner*—Golam M Shameem
(74) *Attorney, Agent, or Firm*—Brinks Hofer Gilson & Lione

(57) ABSTRACT

The present invention relates to 1-(imidazolin-2-yl)amino-1,2-diphenylethane compounds of the formula I and their agriculturally acceptable salts, wherein A is a radical of the formula $A^1$ or $A^2$. The invention relates also to agricultural compositions and to seed comprising at least one compound I and/or a salt thereof, as well as a method of combating animal pests, a method for protecting crops from attack or infestation by animal pests and a method for protecting non-living materials from attack or infestation by animal pests, a method for the protection of seeds from animal pests and of the seedlings' roots and shoots from animal pests by applying a pesticidally effective amount of at least one 1-(imidazolin-2-yl)amino-1,2-diphenylethane compound I and/or a salt thereof.

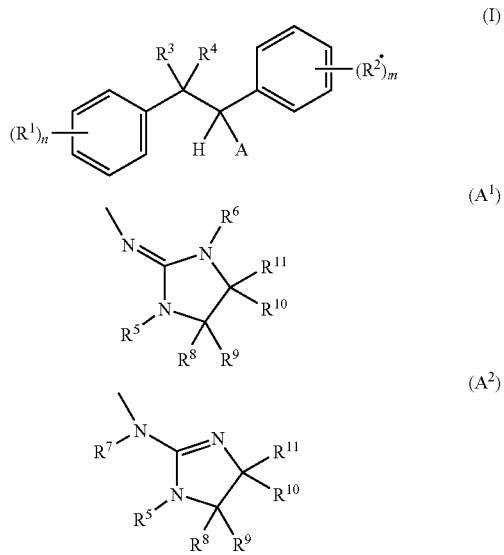

21 Claims, No Drawings

1-(IMIDAZOLIN-2-YL)AMINO-1,2-DIPHENYLETHANE COMPOUNDS FOR COMBATING ANIMAL PESTS

This application is a National Stage application of International Application No. PCT/EP2006/062419, filed May 18, 2006, which claims the benefit of Provisional U.S. Application No. 60/684,122, filed May 24, 2005 and U.S. Provisional Application No. 60/736,714, filed Nov. 15, 2005, the entire contents of which are hereby incorporated herein by reference.

The present invention relates to 1-(imidazolin-2-yl)amino-1,2-diphenylethane compounds which are useful for combating animal pests. The present invention also relates to methods for combating animal pests and to agricultural compositions for combating animal pests.

Animal pests and in particular insects, arachnids and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating insects, arachnids and nematodes.

Compounds similar to those of formula I which, however, bear an isoxazolin-2-ylamino or isothiazolin-2-ylamino radical instead of the imidazolin-2-ylamino radical have already been described as intermediates in WO 2005/63724.

However, these compounds are limited in their activity or with regard to breadth of their activity spectrum.

It is therefore an object of the present invention to provide compounds having a good pesticidal activity and show a broad activity spectrum against a large number of different animal pests, especially against difficult to control insects, arachnids and nematodes.

It has been found that these objectives can be achieved by 1-(imidazolin-2-yl)amino-1,2-diphenylethane compounds of the formula I

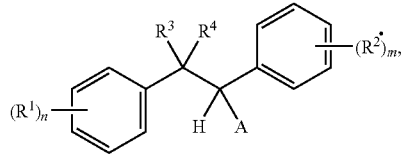

wherein A is a radical of the formulae $A^1$ or $A^2$

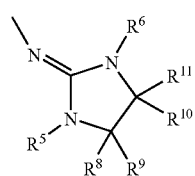

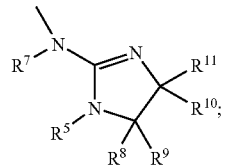

and wherein m is 0, 1, 2, 3, 4 or 5;
n is 0, 1, 2, 3, 4 or 5;
$R^1$, $R^2$ are each independently
 halogen, OH, SH, $NH_2$, $SO_3H$, COOH, cyano, nitro, formyl,
 $C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, ($C_1$-$C_6$-alkyl)carbonyl, ($C_2$-$C_6$-alkenyl)carbonyl, ($C_2$-$C_6$-alkynyl)carbonyl, ($C_1$-$C_6$-alkoxy)carbonyl, ($C_2$-$C_6$-alkenyloxy)carbonyl, ($C_2$-$C_6$-alkynyloxy)carbonyl, ($C_1$-$C_6$-alkyl)carbonyloxy, ($C_2$-$C_6$-alkenyl)carbonyloxy or ($C_2$-$C_6$-alkynyl)carbonyloxy,
 wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
 $C(O)NR^aR^b$, $(SO_2)NR^aR^b$, a radical Y—Ar or a radical Y-Cy, wherein
Y is a single bond, oxygen, sulfur, $C_1$-$C_6$-alkandiyl or $C_1$-$C_6$-alkandiyloxy;
Ar is phenyl, naphthyl or a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Ar is unsubstituted or may carry any combination of 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; and
Cy is $C_3$-$C_{12}$-cycloalkyl, which is unsubstituted or substituted with 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
and wherein two radicals $R^1$ or two radicals $R^2$ that are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

$R^3$, $R^4$ are each independently hydrogen, $C_1$-$C_6$-alkyl, $C_1$-$C_6$-haloalkyl or $C_3$-$C_6$-cycloalkyl, wherein the carbon atoms in the last 3 groups may carry any combination of 1, 2 or 3 radicals, independently of one another selected from the group consisting of cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or phenyl or benzyl, each unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;

$R^5$, $R^6$ are each independently hydrogen, cyano, nitro, formyl, $C_1$-$C_6$-alkyl, ($C_1$-$C_6$-alkyl)carbonyl, ($C_1$-$C_6$-alkoxy)carbonyl, ($C_1$-$C_6$-alkylthio)carbonyl or ($C_1$-$C_6$-alkoxy)methylen, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or $C(O)NR^cR^d$, $(SO_2)NR^cR^d$, phenyl, phenyloxy or benzyl, each of the last three mentioned radicals may be unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;

$R^7$ is hydrogen, cyano, nitro, formyl, $C_1$-$C_6$-alkyl, ($C_1$-$C_6$-alkyl)carbonyl, ($C_1$-$C_6$-alkoxy)carbonyl, ($C_1$-$C_6$-alkylthio)carbonyl or ($C_1$-$C_6$-alkoxy)methylen, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or $R^7$ is $C(O)NR^eR^f$ or $(SO_2)NR^eR^f$, phenyl, phenyloxy or benzyl, each of the last three mentioned groups may be unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;

$R^8$, $R^9$, $R^{10}$, $R^{11}$ are each independently hydrogen, $C_1$-$C_6$-alkyl, $C_1$-$C_6$-haloalkyl, $C_1$-$C_6$-alkylamino, $C_1$-$C_6$-alkoxy or $C_3$-$C_6$-cycloalkyl, wherein the carbon atoms of the last 5 groups may carry any combination of 1, 2 or 3 radicals, independently of one another selected, from the group consisting of cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

$R^a$, $R^b$, $R^c$, $R^d$, $R^e$, $R^f$ are, independently of one another, hydrogen, $C_1$-$C_6$-alkyl, $C_1$-$C_6$-haloalkyl, $C_2$-$C_6$-alkenyl or $C_2$-$C_6$-alkynyl;

and the agriculturally acceptable salts thereof.

Therefore, the present invention relates to 1-(imidazolin-2-yl)amino-1,2-diphenylethane compounds of the formula I and to the agriculturally acceptable salts thereof. These compounds have a high pesticidal activity and are active against a broad spectrum of animal pests, especially against insects, arachnids and nematodes.

The invention also relates to a method of combating animal pests, especially insects, arachnids and nematodes, which comprises contacting the animal pests, their habit, breeding ground, food supply, plant, seed, soil, area, material or environment in which the animal pests are growing or may grow, or the materials, plants, seeds, soils, surfaces or spaces to be protected from attack or infestation by the animal pests, especially insects, arachnids or nematodes, with a pesticidally effective amount of at least one 1-(imidazolin-2-yl)amino-1,2-diphenylethane compound of the formula I and/or at least one agriculturally acceptable salt thereof to a method for the protection of seeds from animal pests and of the seedlings' roots and shoots from animal pests, and to seed comprising a compound of the formula I or an agriculturally acceptable salt of I.

Furthermore, the present invention provides a method for protecting crops from attack or infestation by animal pests, especially insects, arachnids or nematodes, which comprises contacting a crop with a pesticidally effective amount of at least one 1-(imidazolin-2-yl)amino-1,2-diphenylethane compound of the formula I and/or at least one salt thereof.

Furthermore, the invention relates to agricultural compositions, preferably in the form of directly sprayable solutions, emulsions, pastes oil dispersions, powders, materials for scattering, dusts or in the form of granules, which comprise at least one 1-(imidazolin-2-yl)amino-1,2-diphenylethane compound of the formula I as defined above or a salt thereof, admixed with one or more agronomically acceptable inert, solid or liquid carrier(s) and, if desired, at least one surfactant.

The compounds of the formula I may have one or more centers of chirality, in which case they are present as mixtures of stereoisomers, such as enantiomers or diastereomers. The present invention provides both the pure stereoisomers, e.g. the pure enantiomers or diastereomers, and mixtures thereof. The compounds of the formula I may also exist in the form of different tautomers. The invention comprises the single tautomers, if seperable, as well as the tautomer mixtures.

Salts of the compounds of the formula I which are suitable for the use according to the invention are especially agriculturally acceptable salts. They can be formed in a customary method, e.g. by reacting the compound with an acid of the anion in question if the compound of formula I has a basic functionality or by reacting an acidic compound of formula I with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl and/or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

Examples of other meanings are:

The term "$C_1$-$C_6$-alkyl" as used herein and in the alkyl moieties of $C_1$-$C_6$-alkoxy, $C_1$-$C_6$-alkylamino, di($C_1$-$C_6$-alkyl)amino, $C_1$-$C_6$-alkylthio, $C_1$-$C_6$-alkylsulfonyl, $C_1$-$C_6$-alkylsulfoxyl, ($C_1$-$C_6$-alkyl)carbonyl, ($C_1$-$C_6$-alkoxy)carbonyl, ($C_1$-$C_6$-alkylthio)carbonyl, and ($C_1$-$C_6$-alkyl)carbonyloxy refer to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term, "$C_1$-$C_6$-alkoxy" as used herein refers to a straight-chain or branched saturated alkyl group having 1 to 6 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_1$-$C_6$-alkoxy-$C_1$-$C_6$-alkyl" as used herein refers to $C_1$-$C_6$-alkyl wherein 1 carbon atom carries a $C_1$-$C_6$-alkoxy radical as mentioned above. Examples are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "($C_1$-$C_6$-alkyl)carbonyl" as used herein refers to a straight-chain or branched saturated alkyl group having 1 to 6 carbon atoms (as mentioned above) bonded via the carbon atom of the carbonyl group at any bond in the alkyl group. Examples include $C_1$-$C_6$-alkylcarbonyl such $CO$—$CH_3$, $CO$—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "($C_1$-$C_6$-alkoxy)carbonyl" as used herein refers to a straight-chain or branched alkoxy group (as mentioned above) having 1 to 6 carbon atoms attached via the carbon atom of the carbonyl group, for example CO—OCH$_3$, CO—OC$_2$H$_5$, COO—CH$_2$—C$_2$H$_5$, CO—OCH(CH$_3$)$_2$, n-butoxycarbonyl, CO—OCH(CH$_3$)—C$_2$H$_5$, CO—OCH$_2$—CH(CH$_3$)$_2$, CO—OC(CH$_3$)$_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl.

The term "($C_1$-$C_6$-alkyl)carbonyloxy" as used herein refers to a straight-chain or branched saturated alkyl group having 1 to 6 carbon atoms (as mentioned above) bonded via the carbon atom of the carbonyloxy group at any bond in the alkyl group, for example O—CO—CH$_3$, O—CO—C$_2$H$_5$, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy or 1,2-dimethylpropylcarbonyloxy.

The term "$C_1$-$C_6$-alkylthio ($C_1$-$C_6$-alkylsulfanyl: $C_1$-$C_6$-alkyl-S—)" as used herein refers to a straight-chain or branched saturated alkyl group having 1 to 6 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio, 1,1-dimethylethylthio, n-pentylthiocarbonyl, 1-methyl butylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylhio, 2,2-dimethylbutylthio, 2,3-dimethylbutylthio, 3,3-dimethylbutylthio, 1-ethylbutithio, 2-ethylbutylthio, 1,1,2-trimethylpropylthio, 1,2,2-trimethylpropylthio, 1-ethyl-1-methylpropylthio or 1-ethyl-2-methylpropylthio.

The term "($C_1$-$C_6$-alkylthio)carbonyl" as used herein refers to a straight-chain or branched alkthio group (as mentioned above) having 1 to 6 carbon atoms attached via the carbon atom of the carbonyl group. Examples include CO—SCH$_3$, CO—SC$_2$H$_5$, CO—SCH$_2$—C$_2$H$_5$, CO—SCH(CH$_3$)$_2$, n-butylthiocarbonyl, CO—SCH(CH$_3$)—C$_2$H$_5$, CO—SCH$_2$—CH(CH$_3$)$_2$, CO—SC(CH$_3$)$_3$, n-pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, n-hexylthiocarbonyl, 1,1-dimethylpropylthiocarbonyl, 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutylhiocarbonyl, 2,2-dimethylbutylthiocarbonyl, 2,3-dimethylbutylthiocarbonyl, 3,3-dimethylbutylthiocarbonyl, 1-ethylbutylthiocarbonyl, 2-ethylbutylthiocarbonyl, 1,1,2-trimethylpropylthiocarbonyl, 1,2,2-trimethylpropylthiocarbonyl, 1-ethyl-1-methylpropylthiocarbonyl or 1-ethyl-2-methylpropylthiocarbonyl.

The term "$C_1$-$C_6$-alkylsulfinyl" ($C_1$-$C_6$-alkylsulfoxyl: $C_1$-$C_6$-alkyl-S($=$O)—), as used herein refers to a straight-chain or branched saturated hydrocarbon group (as mentioned above) having 1 to 6 carbon atoms bonded through the sulfur atom of the sulfinyl group at any bond in the alkyl group, for example SO—CH$_3$, SO—C$_2$H$_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-di-methylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethyl-butylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_6$-alkylamino" refers to a secondary amino group carrying one alkyl group as defined above, e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino.

The term "di($C_1$-$C_6$-alkyl)amino" refers to a tertiary amino group carrying two alkyl radicals as defined above, e.g. dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, N-(n-pentyl)-N-methylamino, N-(n-propyl)-N-ethylamino, N-(isopropyl)-N-ethylamino, N-(n-butyl)-N-ethylamino, N-(n-pentyl)-N-ethylamino, N-(2-butyl)-N-ethylamino, N-(isobutyl)-N-ethylamino or N-(n-pentyl)-N-ethylamino.

The term "$C_1$-$C_6$-alkylsulfonyl" ($C_1$-$C_6$-alkyl-S($=$O)$_2$—) as used herein refers to a straight-chain or branched saturated alkyl group having 1 to 6 carbon atoms (as mentioned above) which is bonded via the sulfur atom of the sulfonyl group at any bond in the alkyl group, for example $SO_2$—$CH_3$, $SO_2$—$C_2H_5$, n-propylsulfonyl, $SO_2$—$CH(CH_3)_2$, n-butylsulfonyl, 1-methylpropylsulfonyl, 2-methylpropylsulfonyl, $SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl.

The term "$C_2$-$C_6$-alkenyl" as used herein and in the alkenyl moieties of $C_2$-$C_6$-alkenyloxy, $C_2$-$C_6$-alkenylamino, $C_2$-$C_6$-alkenylthio, $C_2$-$C_6$-alkenylsulfonyl, ($C_2$-$C_6$-alkenyl)carbonyl, ($C_2$-$C_6$-alkenyloxy)carbonyl and ($C_2$-$C_6$-alkenyl)carbonyloxy refers to a straight-chain or branched unsaturated hydrocarbon group having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term, "$C_2$-$C_6$-alkenyloxy" as used herein refers to a straight-chain or branched saturated alkenyl group having 2 to 6 carbon atoms (as mentioned above) which is attached via an oxygen atom, such as vinyloxy, allyloxy(propen-3-yloxy), methallyloxy, buten-4-yloxy, etc.

The term "$C_2$-$C_6$-alkenylthio" as used herein refers to a straight-chain or branched saturated alkenyl group having 2 to 6 carbon atoms (as mentioned above) which is attached via a sulfur atom, for example vinylsulfanyl, allylsulfanyl(propen-3-ylthio), methallylsufanyl, buten-4-ylsulfanyl, etc.

The term "$C_2$-$C_6$-alkenylamino" as used herein refers to a straight-chain or branched saturated alkenyl group having 2 to 6 carbon atoms (as mentioned above) which is attached via a sulfur atom, for example vinylamino, allylamino(propen-3-ylamino), methallylamino, buten-4-ylamino, etc.

The term "$C_2$-$C_6$-alkenylsulfonyl" as used herein refers to a straight-chain or branched saturated alkenyl group having 2 to 6 carbon atoms (as mentioned above) which is attached via a sulfonyl ($SO_2$) group, for example vinylsulfonyl, allylsulfonyl (propen-3-ylsulfonyl), methallylsulfonyl, buten-4-ylsulfonyl, etc.

The term "$C_2$-$C_6$-alkynyl" as used herein and in the alkynyl moieties of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl and $C_1$-$C_6$-alkynylcarbonyloxy refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term, "$C_2$-$C_6$-alkynyloxy" as used herein refers to a straight-chain or branched saturated alkynyl group having 2 to 6 carbon atoms (as mentioned above) which is attached via an oxygen atom, such as propargyloxy(propin-3-yloxy), butin-3-yloxy, and butin-4-yloxy.

The term "$C_2$-$C_6$-alkynylthio" as used herein refers to a straight-chain or branched saturated alkynyl group having 2 to 6 carbon atoms (as mentioned above) which is attached via a sulfur atom, such as propargylsulfanyl (propin-3-ylthio), butin-3-ylsufanyl and butin-4-ylsulfanyl.

The term "$C_2$-$C_6$-alkynylamino" as used herein refers to a straight-chain or branched saturated alkynyl group having 2 to 6 carbon atoms (as mentioned above) which is attached via a sulfur atom, such as propargylamino(propin-3-ylamino), butin-3-amino, and butin-4-ylamino.

The term "$C_2$-$C_6$-alkynylsulfonyl" as used herein refers to a straight-chain or branched saturated alkynyl group having 2 to 6 carbon atoms (as mentioned above) which is attached via a sulfonyl ($SO_2$) group, such as propargylsulfonyl (propin-3-ylsulfonyl), butin-3-ylsulfonyl and butin-4-ylsulfonyl.

The term "$C_3$-$C_{12}$-cycloalkyl" as used herein refers to a mono- or bi- or polycyclic hydrocarbon radical having 3 to 12 carbon atoms, in particular 3 to 6 carbon atoms. Examples of monocyclic radicals comprise cyclopropyl, cyclobutyl, cyclopentyl, cyclohexyl, cycloheptyl, cyclooctyl, cyclononyl and cyclodecyl. Examples of bicyclic radicals comprise bicyclo[2.2.1]heptyl, bicyclo[3.1.1]heptyl, bicyclo[2.2.2]octyl and bicyclo[3.2.1]nonyl. Examples of tricylcic radicals are adamantyl and homoadamantyl.

The term "mono- or bicylcic heteroaromatic ring" as used herein refers to a monocyclic heteroaromatic radical which has 5 or 6 ring members, which may comprise a fused 5, 6 or 7 membered ring thus having a total number of ring members from 8 to 10, wherein in each case 1, 2, 3 or 4 of these ring members are heteroatoms selected, independently from each other, from the group consisting of oxygen, nitrogen and sulfur. The heterocyclic radical may be attached to the remainder of the molecule via a carbon ring member or via a nitrogen ring member. The fused ring comprises $C_5$-$C_7$-cycloalkyl, $C_5$-$C_7$-cycloalkenyl, or 5 to 7 membered heterocyclyl and phenyl.

Examples for monocyclic 5- to 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

Examples for 5- to 6-membered heteroaromatic rings carrying a fused phenyl ring are quinolinyl, isoquinolinyl, indolyl, indolizinyl, isoindolyl, indazolyl, benzofuryl, benzthienyl, benzo[b]thiazolinyl, benzoxazolyl, benzthiazolyl, benzoxazolyl, and benzimidazolyl. Examples for 5- to 6-membered heteroaromatic rings carrying a fused cycloalkenyl ring are dihydroindolyl, dihydroindolizinyl, dihydroisoindolyl, dihydrochinolinyl, dihydroisochinolinyl, chromenyl, chromanyl and the like.

The term "5 to 7 membered heterocyclyl" comprises monocyclic heteroaromatic rings as defined above and non-aromatic saturated or partially unsaturated heterocyclic rings having 5, 6 or 7 ring members. Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

As regards the pesticidal activity of the compounds of formula I, preference is given to those compounds of formula I, in which the variables—independently of one another or in combination with any of the other variables—have the following meanings:

$n$ is 1, 2 or 3;
$m$ is 1, 2 or 3;
$m+n = 1, 2, 3, 4, 5$ or $6$, especially 2, 3, 4 or 5;
$R^3$ hydrogen or $C_1$-$C_4$-alkyl, especially hydrogen or methyl and most preferred hydrogen;
$R^4$ hydrogen, $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;
$R^5$ hydrogen, cyano, formyl, $C_1$-$C_4$-alkyl, $C_1$-$C_6$-alkylcarbonyl, $C_1$-$C_4$-haloalkylcarbonyl, $C_1$-$C_6$-alkoxycarbonyl, $C_1$-$C_6$-alkylthiocarbonyl or ($C_1$-$C_6$-alkoxy)methylen;
$R^6$ hydrogen, cyano, formyl, $C_1$-$C_4$-alkyl, $C_1$-$C_6$-alkylcarbonyl, $C_1$-$C_4$-haloalkylcarbonyl, $C_1$-$C_6$-alkoxycarbonyl, $C_1$-$C_6$-alkylthiocarbonyl or ($C_1$-$C_6$-alkoxy)methylen;
$R^7$ hydrogen;
$R^8$, $R^9$, $R^{10}$ and $R^{11}$ are each hydrogen, or one of these radicals may also be $C_1$-$C_4$-alkyl;
$R^a$, $R^b$, $R^c$, $R^d$, $R^e$, $R^f$ are, independently of one another, hydrogen or $C_1$-$C_6$-alkyl.

In a very preferred embodiment of the invention both radicals $R^3$ and $R^4$ are hydrogen. In another preferred embodiment of the invention $R^3$ is hydrogen and $R^4$ is selected from $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups. In this embodiment $R^4$ is preferably methyl, ethyl or especially unsubstituted or substituted phenyl.

Amongst compounds I, preference is given to those wherein A is a radical of formula $A^2$, in particular compounds of the formula I with A being $A^2$, wherein $R^7$ is =H. If, in these compounds, $R^5$ is also hydrogen, they are autoners of the compounds I with A being $A^1$, wherein $R^5$ and $R^6$ are hydrogen. These tautomers are present as their equilibrium mixture.

The compounds of the present invention can be e.g. prepared from the corresponding diphenylethylamines II by the synthetic routes outlined in Schemes 1 and 2.

Compounds of the formula I, wherein A is a radical $A^2$ and $R^5$ and $R^7$ are hydrogen, can be obtained according to the method outlined in Scheme 1.

Scheme 1:

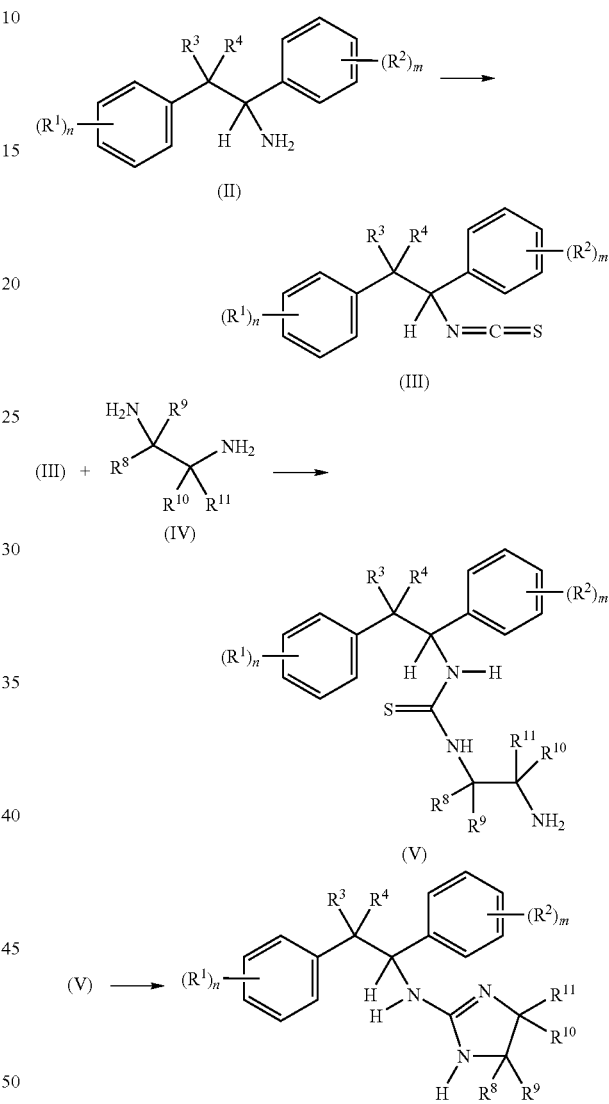

According to the method outlined in Scheme 1, a 1,2-diphenylaminoethane II can be converted into the corresponding isothiocyanate III by conventional means, e.g. by reacting II with thiophosgene (see e.g. Houben-Weyl, E4, "Methoden der Organischen Chemie", chapter IIIc, pp. 837-842, Georg Thieme Verlag 1983.

The isothiocyanate III is then reacted with a 1,2 diaminoethane of the formula IV, thereby obtaining the thiourea compound of the formula V. This reaction can be performed in accordance with standard methods of organic chemistry, see e.g. Tetrahedron 60, 9883-9888 (2004).

The thus obtained thioureas (V) can be cyclized by conventional means, thereby obtaining the desired compound of the formula I, wherein A is $A^2$ with $R^5$ and $R^7$ being hydrogen. Cyclization of compound (V) can be achieved e.g. via intermediate carbodiimide formation and amine addition with e.g. Tosylchloride/NaOH (see, for example Tetrahedron 60, 9883-9888 (2004)) or yellow mercury(II) according to Synthesis, 482-484 (1982).

The 1,2-diphenylaminoethanes II and their preparation are known from the literature or said compounds can be prepared by conventional methods.

Compounds of the formula I, wherein A is a radical of the formula $A^2$ with $R^5$ and $R^7$ being hydrogen, can also be obtained by the method outlined in Scheme 2.

Scheme 2:

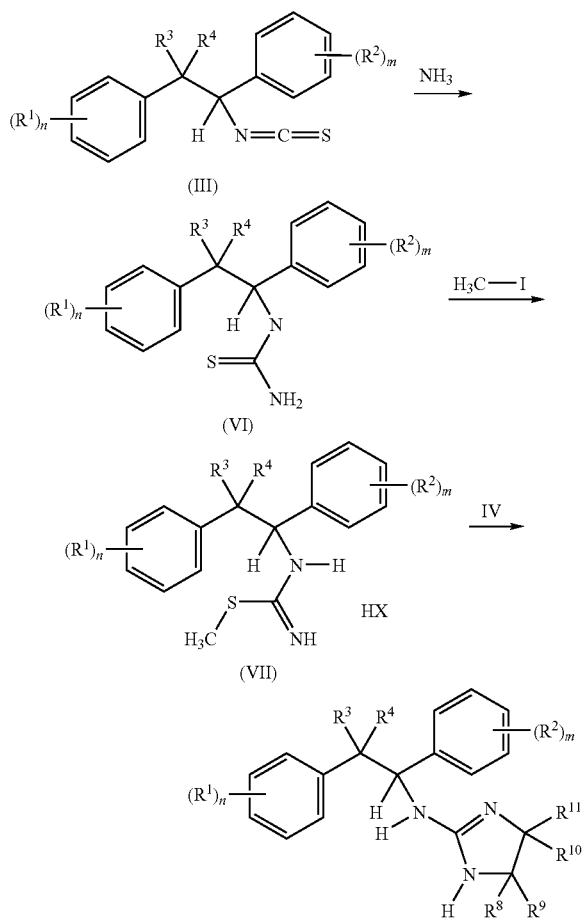

The isothiocyanate III is converted to the corresponding thiourea VI, which subsequently is treating with methyl iodide to yield the isothiuronium salt VII. Finally, the intermediate VII is reacted with 1,2-diaminoethane (see for example U.S. Pat. No. 2,899,426).

Compounds of formula I can also be obtained
- by reacting a 1,2-diphenylaminoethane II with a 2-substituted imidazoline in an appropriate solvent as for example described for the synthesis of clonidin in U.S. Pat. No. 5,130,441,
- by reacting imidazoline-2-sulfonic acid with 2,6-dichloroanilin in isobutanol,
- by reacting a 1,2-diphenylaminoethane II with 2-methylthioimidazoline hydroiodide as described in EP-A 389765 (see Example 5),
- by reacting a diphenylaminoethane II with a 2-halo-1,3-disubstituted imidazoline or imidazolinium salt, e.g. as demonstrated for the reaction of 2-chloro-1,3-dimethylimidazolinium chloride with amines in T. Isobe et al., Tetrahedron Asymmetry 9, 1729-1735 (1998), e.g. for the preparation of compound 3a.

The particular reaction mixtures are worked up, as a rule, by conventional methods, for example by removing the solvent, distributing the residue in a mixture of water and a suitable organic solvent and isolating the product from the organic phase. If the intermediates and end products are obtained as solids, they may be purified by recrystallization or digestion.

The 1-(imidazolin-2-yl)amino-1,2-diphenylethane compounds I may be obtained in the preparation as isomer mixtures, which however can, if desired, be separated into the pure isomers by conventional methods, for example by crystallization or chromatography (if necessary, over an optically active adsorbate). Pure optically active isomers can be synthesized, for example, from corresponding optically active starting materials.

As a rule, the 1-(imidazolin-2-yl)amino-1,2-diphenylethane compounds of the formula I can be prepared by the methods described above. However, in individual cases, certain compounds I can also advantageously be prepared from other compounds I by derivatization or by customary modifications of the synthesis routes described above, for example by ester hydrolysis, amidation, esterification, ether cleavage, olefination, reduction, oxidation, cross-coupling reactions or cyclization reactions at the positions of the radical $R^1$ or $R^2$ or by ester hydrolysis, transesterification, ether cleavage or oxidation at the positions of the radical $R^5$, $R^6$ or $R^7$.

Due to their excellent activity, the compounds of the formula I may be used for controlling animal pests, in particular selected harmful insects, arachnids and nematodes. Accordingly, the invention further provides agriculturally composition for combating such animal pests, which comprises such an amount of at least one compound of the formula I or at least an agriculturally useful salt of I and at least one inert liquid and/or solid agronomically acceptable carrier that it has a pesticidal action and, if desired, at least one surfactant.

Such a composition may contain a single active compound of the formula I or a mixture of several active compounds I according to the present invention. The composition according to the present invention may comprise an individual isomer or mixtures of isomers as well as individual tautomers or mixtures of tautomers.

The compounds of the formula I and the pesticidal compositions comprising them are effective agents for controlling animal pests, particularly those selected from insects, arachnids and nematodes. Animal pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Hellothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar,*

*Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria lilnearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhopfrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria*;

dipterans (Diptera), for example *Aedes aegyptl; Aedes vexans, Anastrepha ludens, Anopheles maculipennis, Ceratitis capitata, Chrysomya bezzlana, Chrysomya hominivorax, Chrysomya macellara, Contarinia sorghicola, Cordylobia anthropophaga, Culex pipiens, Dacus cucurbitae, Dacus oleae, Dasineura brassicae, Fannia canicularis, Gasterophilus intestinalls, Glossina morsitans, Haematobia irritans, Haplodiplosis equestris, Hylemyla platura, Hypoderma lineata, Liriomyza sativae, Liriomyza trifolil, Lucilia caprina, Lucilia cuprina, Lucilia sericata, Lycoria pectoralis, Mayetiola destructor, Musca domestilca, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*;

thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci*;

hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta*;

heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*;

homopterans (Homoptera), e.g. *Acyrthosiphon onobrychis, Adelges laricis, Aphidula nasturtii, Aphis fabae, Aphis forbesi, Aphis porni, Aphis gossypii, Aphis grossulariae, Aphis schneideri, Aphis spiraecola, Aphis sambuci, Acyrthosiphon pisum, Aulacorthum solani, Bernisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasono via ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand*, and *Viteus vitifolii*;

termites (Isoptera), e.g. *Calotermes flavicollis, Leucotermes flavipes, Reticulitermes flavipes, Reticulitermes lucifugus* und *Termes natalensis*;

orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*;

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocopfrata oleivora and Eriophyes sheldoni*; Tarsonemidae spp. such as *Phytonemus pallidus* and *Polyphagotarsonemus latus*, Tenuipalpidae spp. such as *Brevipalpus phoenicis*, Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and *oligonychus pratensis*;

Siphonatera, e.g. *Xenopsylla cheopsis, Ceratophyllus* spp;

The compositions and compounds of formula I are useful for the control of nematodes, especially plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera and Homoptera and arachnids of the order Acarina. The compounds of the formula I according to the present invention are particularly useful for controlling insects of the order Lepidoptera and Homoptera.

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

For use according to the present invention, the compounds I can be converted into the customary formulations, e.g. solutions, emulsions, suspensions, dusts, powders, pastes and granules. The use form depends on the particular purpose; it is intended to ensure in each case a fine and uniform distribution of the compound according to the invention.

The pesticidal composition for combating animal pests, i.e. insects, arachnids, or nematodes, contains such an amount of at least one compound of the general formula I or an agriculturally useful salt of I and auxiliaries which are usually used in formulating pesticidal composition.

The formulations are prepared in a known manner, e.g. by extending the active ingredient with solvents and/or carriers, if desired using emulsifiers and dispersants. Solvents/auxiliaries, which are suitable, are essentially:

water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:
1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulations (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is mostly done by dipping the textile material into emulsions or dispersions of the insecticide or by spraying them onto the nets.

The compounds of formula I are also suitable for the treatment of seeds. Conventional seed treatments include for example flowable concentrates FS, solutions LS, powders for dry treatment DS, water dispersible powders for slurry treatment WS, water soluble powders SS and emulsion ES. Application to the seeds is carried out before sowing, either directly on the seeds or after having pregerminated the latter.

Preferred FS formulations of compounds of formula I for seed treatment comprise from 0.5 to 80% of the active ingredient, from 0.05 to 5% of a wetter, from 0.5 to 15% of a dispersing agent, from 0.1 to 5% of a thickener, from 5 to 20% of an anti-freeze agent, from 0.1 to 2% of an anti-foam agent, from 1 to 20% of a pigment and/or a dye, from 0 to 15% of a sticker/adhesion agent, from 0 to 75% of a filler/vehicle, and from 0.01 to 1% of a preservative.

Stickers/adhesion agents are added to improve the adhesion of the active materials on the seeds after treatment. Suitable adhesives are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers and copolymers derived from these polymers.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds I or the compositions comprising them in the use form as pesticides with other pesticides frequently results in a broader pesticidal spectrum of action.

The following list of pesticides together with which the compounds of formula I can be used, is intended to illustrate the possible combinations, but not to impose any limitation:

Organo(thio)phosphates: Acephate, Azamethiphos, Azinphos-methyl, Chlorpyrifos, Chlorpyrifos-methyl, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Suiprophos, Tetrachlorvinphos, Terbufos, Triazophos, Trichlorfon;

Carbamates: Alanycarb, Bendiocarb, Benfuracarb, Carbaryl, Carbofuran, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Allethrin, Bifenthrin, Cyfluthrin, Cyhalothrin, Cyphenothrin, Cypermethrin, alpha-Cypermethrin, beta-Cypermethrin, zeta-Cypermethrin Deltamethrin, Esfenvalerate, Ethofenprox, Fenpropathrin, Fenvalerate, Imiprothrin, Lambda-Cyhalothrin, Permethrin, Prallethrin, Pyrethrin I and II, Silafluofen, Tau-Fluvalinate, Tefluthrin, Tetramethrin, Tralomethrin, Transfluthrin;

Growth regulators: a) chitin synthesis inhibitors: benzoylureas: Chlorfluazuron, Cyramazin, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen, Spiromesifen, tetronic acid derivatives of formula VIII,

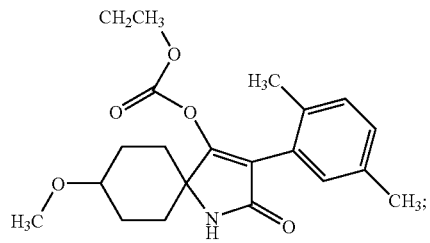

Neonicotinoids: Clothianidine, Dinotefuran, Imidacloprid, Thiamethoxam, Nitenpyram, Nithiazine, Acetamiprid, Thiacloprid;

Pyrazole pesticides: Acetoprole, Ethiprole, Fipronil, Tebufenpyrad, Tolfenpyrad, Vaniliprole;

Various: Abamectin, Acequinocyl, Amidoflumet, Amitraz, Azadirachtin, Benclothiaz, Bifenazate, Bistrifluoron, Cartap, Chlorfenapyr, Chlordimeform, Cyflumetofen, Cyromazine, Diafenthiuron, Dimefluthrin, Diofenolan, Emamectin, Endosulfan, Fenazaquin, Flonicamid, Fluacyprim, Flubendiamide, Flufenerim, Flupyrazofos, Formetanate, Formetanate hydrochloride, Hydramethylnon, Indoxacarb, Lepimectin, Metaflumizone, Milbemectin, Piperonylbutoxide, Profluthrin, Pyridaben, Pyridalyl, Pymetrozine, Pyrafluprole, Pyriprole, Spinosad, Spirotetramat, Sulfur, Tebufenpyrad, Thiocyclam, Tolfenpyrad and the aminoisothiazole compound of formula IX,

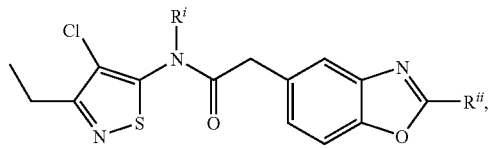

wherein $R^i$ is hydrogen or —CH$_2$OCH$_3$ and $R^{ii}$ is —CF$_2$CF$_2$CF$_3$, anthranilamide compounds of formula X

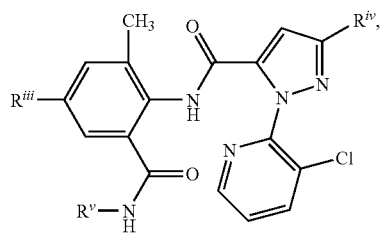

wherein $R^{iii}$ is hydrogen or a chlorine atom, $R^{iv}$ is a bromine atom or CF$_3$ and $R^v$ is C$_1$-C$_6$-alkyl, and malononitrile compounds as described in JP 2002/284608, WO 02/89579, WO 02/90320, WO 02/90321, WO 04/06677, WO 04/20399 or JP 2004/099597.

Fungicidal mixing partners are those selected from the group consisting of
acylalanines such as benalaxyl, metalaxyl, ofurace, oxadixyl,
amine derivatives such as aldimorph, dodine, dodemorph, fenpropimorph, fenpropidin, guazatine, iminoctadine, spiroxamin, tridemorph,
anilinopyrimidines such as pyrimethanil, mepanipyrim or cyrodinyl,
antibiotics such as cycloheximid, griseofulvin, kasugamycin, natamycin, polyoxin or streptomycin,
azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol,
dicarboximides such as iprodion, myclozolin, procymidon, vinclozolin,
dithiocarbamates such as ferbam, nabam, maneb, mancozeb, metam, metiram, propineb, polycarbamate, thiram, ziram, zineb,
heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine,
copper fungicides such as Bordeaux mixture, copper acetate, copper oxychloride, basic copper sulfate,
nitrophenyl derivatives such as binapacryl, dinocap, dinobuton, nitrophthalisopropyl,
phenylpyrroles such as fenpiclonil or fludioxonil,
sulfur,
other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid,
strobilurins such as azoxystrobin, dimoxystrobin, fluoxastrobin, kresoxim-methyl, metominostrobin, orysastrobin, picoxystrobin or trifloxystrobin,
sulfenic acid derivatives such as captafol, captan, dichlofluanid, folpet, tolyifluanid,
cinnemamides and analogs such as dimethomorph, flumetover or flumorph.

The animal pest, i.e. the insects, arachnids and nematodes, the plant, soil or water in which the plant is growing can be contacted with the present compound(s) I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the urider-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

The aforementioned compositions are particularly useful for protecting crop plants against infestation of said pests or for combating these pests in infested plants.

For use in treating crop plants, the rate of application of the active ingredients of this invention may be in the range of 0.1 g to 4000 g per hectare, desirably from 25 g to 600 g per hectare, more desirably from 50 g to 500 g per hectare.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.001 weight % to 15 weight %, desirably from 0.001 weight % to 5 weight % of active compound.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Compositions which are especially useful for seed treatment are e.g.:

A Water soluble concentrates (SL, LS)

D Emulsions (EW, EO, ES)

E Suspensions (SC, OD, FS)

F Water-dispersible granules and water-soluble granules (WG, SG)

G Water-dispersible powders and water-soluble powders (WP, SP, SS, WS)

H Gel-Formulations (GF)

I Dustable powders (DP, DS)

The compounds of formula I are also suitable for the treatment of seeds. Conventional seed treatments include for example flowable concentrates FS, solutions LS, powders for dry treatment DS, water dispersible powders for slurry treatment WS, water soluble powders SS and emulsion ES. Application to the seeds is carried out before sowing, either directly on the seeds or after having pregerminated the latter.

Preferred FS formulations of compounds of formula I for seed treatment usually comprise from 0.1 to 80% by weight (1 to 800 g/L) of the active ingredient, from 0.1 to 20% by weight (1 to 200 g/L) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, anti-oxidant or the like, e.g. in an amount from 0.01 to 1% by weight and a filler/vehicle up to 100% by weight.

Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Binders, which are also referred to as stickers/adhesion agents are added to improve the adhesion of the active materials on the seeds after treatment. Suitable adhesives are block copolymers EO/PO surfactants but also polyvinylalcohols, polyvinylpyrrolidones, polyacrylates, polymethacrylates, polybutenes, polyisobutylenes, polystyrene, polyethylene-amines, polyethyleneamides, polyethyleneimines (Lupasol®, Polymin®), polyethers and copolymers derived from these polymers.

In the treatment of seed, the application rates of the compounds I are generally from 0.1 g to 10 kg per 100 kg of seed, preferably from 1 g to 5 kg per 100 kg of seed, in particular from 1 g to 1000 g per 100 kg of seed.

The invention therefore also relates to seed comprising a compound of the formula I or an agriculturally useful salt of 1, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5 weight % of active compound.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

The present invention is now illustrated in further detail by the following examples.

1. EXAMPLES OF PREPARATION OF COMPOUNDS

Example P.1

[2-(3-Chloro-phenyl)-1-phenyl-ethyl]-(4,5-dihydro-1H-imidazol-2-yl)-amine hydroiodide

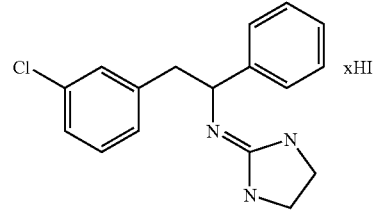

1.22 g (5.00 mmol) 2-methylsulfanyl-4,5-dihydro-1H-imidazole were added at room temperature to a solution of 1.16 g (5.00 mmol) 2-(3-chloro-phenyl)-1-phenylethylamine in n-pentanol and heated to reflux for 2 hours. The reaction mixture was cooled down and concentrated under reduced pressure. Treatment with a small portion of ethyl acetate caused precipitation. The precipitate was filtered off and dried under reduced pressure to yield 0.85 g (1.99 mmol, 40%) of the desired compound.

Example P.2

1-[2-(1,2-Diphenylethylamino)-4,5-dihydroimidazol-1-yl]-ethanone (Compound 2.1)

A mixture of 457 mg (4,5-dihydro-1H-imidazol-2-yl)-(1,2-diphenylethyl)-amine hydroiodide (1.16 mmol) and 400 mg potassium carbonate (2.9 mmol) in 20 ml dimethylformamid was treated with 83 mg acetyl chloride (1.06 mmol) and heated up to 50° C. for 6 hours. Aqueous work-up with ethyl acetate and water yielded a crude that was purified by column chromatography on silica gel to give 70 mg product (0.23 mmol, 22%).

The compounds of the formula Ia and Ib can be prepared accordingly. The physicochemical data of these compounds are listed in Table 1 and 2.

TABLE 1

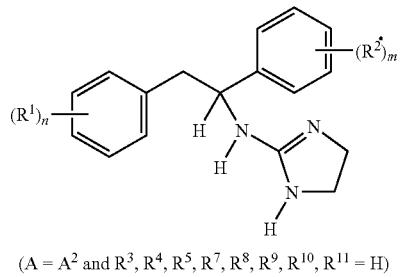

Ia $(A = A^2$ and $R^3, R^4, R^5, R^7, R^8, R^9, R^{10}, R^{11} = H)$

| Ex. | $(R^1)_m$ | $(R^2)_n$ | Physico-chemical data (m.p. [° C.]; $^1$H-NMR (CDCl$_3$): δ [ppm]) |
|---|---|---|---|
| 1.1 HI-salt | 3-Cl | — | m.p. 162-164° C. |
| 1.2 HI-salt | 4-Cl | — | 3.0-3.4 (m), 4.85 (mc), 6.1 (br s), 7.2-7.4 (m), 8.4 (br s), 8.9 (d) |
| 1.3 HI-salt | 2-Cl, 4-F | — | 3.2-3.4 (mc), 4.85 (mc), 5.6 (br s), 6.85-7.45 (m), 7.7 (br s), 9.0 (d) |
| 1.4 free base | 3-Cl | — | 3.05 (mc), 3.5 (m), 4.8 (m), 7.15-7.4 (m), 9.0 (m) |
| 1.5 | 3-F | — | 2.8-3.1 (m), 3.2-4.5 (m), 4.75 (m), 6.9-7.4 (m) |

TABLE 2

Ib $(A = A^2$ and $R^3, R^4, R^7, R^8, R^9, R^{10}, R^{11} = H)$

| Ex. | $(R^1)_m$ | $(R^2)_n$ | $R^5$ | Physico-chemical data (m.p. [° C.]; $^1$H-NMR (CDCl$_3$): δ [ppm]) |
|---|---|---|---|---|
| 2.1 | — | — | acetyl | 2.15 (s), 3.05 (mc), 3.55-3.8 (m), 5.05 (mc), 7.05-7.3 (m), 8.2 (d) |

2. EXAMPLES OF ACTION AGAINST PESTS

The action of the compounds I against pests was demonstrated by the following experiments:

The active compounds were formulated for testing the activity against *Aphis gossypii* and *Myzus persicae*, as 50:50 acetone:water solutions amended with 100 ppm Kinetic® (surfactant), After the experiments were completed, in each case the lowest concentration was determined at which the compound still caused an 50 to 100% inhibition or mortality in comparison with untreated controls (limit or minimal concentration).

Example B.2.1

Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hr. The cotyledons of the intact plants are dipped into gradient solutions of the test compound. Aphid mortality on the treated plants, relative to mortality on check plants, is determined after 5 days.

In this test, compound of example no 1.3 at 300 ppm showed over 80% mortality in comparison with untreated controls.

Example B.2.2

Green Peach Aphid (*Myzus persicae*)

Pepper plants in the 2$^{nd}$ leaf-pair stage (variety 'California Wonder') are infested with approximately 40 laboratory-reared aphids by placing infested leaf sections on top of the test plants. The leaf sections are removed after 24 hr. The leaves of the intact plants are dipped into gradient solutions of the test compound. Aphid mortality on the treated plants, relative to mortality on check plants, is determined after 5 days.

In this test, compounds of example nos 1.3 and 1.5 at 300 ppm showed over 60% mortality in comparison with untreated controls.

Example B.2.3

Vetch Aphid (*Megoura viciae*)

The active compounds were formulated in 1:3 DMSO:water. Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiterplates which were then closed and kept at 22-24° C. and 35-45% under fluorescent light for 6 days. Mortality was assessed on the basis of vital, reproduced aphids. Tests were replicated 2 times.

In this test, compounds of example nos 1.2, 1.5 and 2.1 at 2500 ppm showed over 80% mortality in comparison with untreated controls.

Example B.2.4

Tobacco Budworm (*Heliothis virescens*)

The active compounds were formulated in 1:3 DMSO:water. 15 to 25 eggs were placed into microtiterplates filled with diet. The eggs were sprayed with 10 µl of the test solution, the plates were sealed with pierced foils and kept at 27-29° C. and 75-85% humidity under fluorescent light for 6 days. Mortality was assessed on the basis of the agility of and of comparative feeding of the hatched larvae. Tests were replicated 2 times.

In this test, compound of example no 1.4 at 2500 ppm showed over 80% mortality in comparison with untreated controls.

The invention claimed is:
1. 1-(Imidazolin-2-yl)amino-1,2-diphenylethane compounds of the formula I

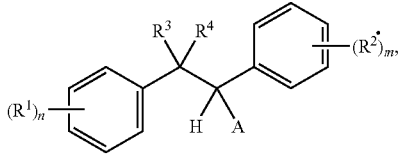

wherein
A is a radical of the formula $A^1$ or $A^2$

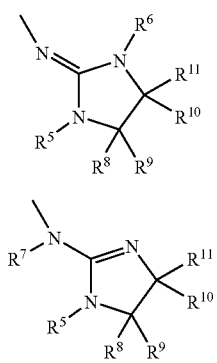

m is 0, 1, 2, 3, 4 or 5;
n is 0, 1, 2, 3, 4 or 5;
$R^1$, $R^2$ are each independently
halogen, OH, SH, $NH_2$, $SO_3H$, COOH, cyano, nitro, formyl,
$C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, ($C_1$-$C_6$-alkyl)carbonyl, ($C_2$-$C_6$-alkenyl)carbonyl, ($C_2$-$C_6$-alkynyl)carbonyl, ($C_1$-$C_6$-alkoxy)carbonyl, ($C_2$-$C_6$-alkenyloxy)carbonyl, ($C_2$-$C_6$-alkynyloxy)-carbonyl, ($C_1$-$C_6$-alkyl)carbonyloxy, ($C_2$-$C_6$-alkenyl)-carbonyloxy or ($C_2$-$C_6$-alkynyl)carbonyloxy,
wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
$C(O)NR^aR^b$, $(SO_2)NR^aR^b$, a radical Y—Ar or a radical Y-Cy, wherein
Y is a single bond, oxygen, sulfur, $C_1$-$C_6$-alkandiyl or $C_1$-$C_6$-alkandiyloxy;
Ar is phenyl, naphthyl or a mono- or bicyclic 5- to 10-membered heteroaromatic ring, which contains 1, 2, 3 or 4 heteroatoms selected from 2 oxygen, 2 sulfur and 3 nitrogen atoms as ring members, wherein Ar is unsubstituted or may carry any combination of 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; and
Cy is $C_3$-$C_{12}$-cycloalkyl, which is unsubstituted or substituted with 1 to 5 radicals, independently of one another selected from the group consisting of halogen, cyano, nitro, hydroxy, mercapto, amino, carboxyl, $C_1$-$C_6$-alkyl, $C_1$-$C_6$-haloalkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
and wherein two radicals $R^1$ or two radicals $R^2$ that are bound to adjacent carbon atoms of the phenyl rings may form, together with said carbon atoms, a fused benzene ring, a fused saturated or partially unsaturated 5-, 6-, or 7-membered carbocycle or a fused 5-, 6- or 7-membered heterocycle, which contains 1, 2, 3 or 4 heteroatoms selected from 2 oxygen, 2 sulfur and 3 nitrogen atoms as ring members, and wherein the fused ring is unsubstituted or may carry 1, 2, 3 or 4 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
$R^3$, $R^4$ are each independently
hydrogen, $C_1$-$C_6$-alkyl, $C_1$-$C_6$-haloalkyl or $C_3$-$C_6$-cycloalkyl, wherein the carbon atoms in the last 3 groups may carry any combination of 1, 2 or 3 radicals, independently of one another selected from the group consisting of cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or
phenyl or benzyl, each unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;
$R^5$, $R^6$ are each independently
hydrogen, cyano, nitro, formyl,
$C_1$-$C_6$-alkyl, ($C_1$-$C_6$-alkyl)carbonyl, ($C_1$-$C_6$-alkoxy)carbonyl, ($C_1$-$C_6$-alkylthio)carbonyl or ($C_1$-$C_6$-alkoxy)methylen, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or
$C(O)NR^cR^d$, $(SO_2)NR^cR^d$, phenyl, phenyloxy or benzyl, each of the last three mentioned radicals may be unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;
$R^7$ is hydrogen, cyano, nitro, formyl, $C_1$-$C_6$-alkyl, ($C_1$-$C_6$-alkyl)carbonyl, ($C_1$-$C_6$-alkoxy)carbonyl, ($C_1$-$C_6$-alkylthio)carbonyl or ($C_1$-$C_6$-alkoxy)methylen, wherein the carbon atoms in the aliphatic radicals of the aforementioned groups may carry any combination of 1, 2 or 3 radicals, independently of one another selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, or $R^7$ is $C(O)NR^eR^f$ or $(SO_2)NR^eR^f$, phenyl, phenyloxy or benzyl, each of the last three mentioned groups may be unsubstituted or substituted with 1 to 5 radicals, independently of one another selected from the group consisting of 5 halogen radicals, 3 $C_1$-$C_o$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals;

$R^8$, $R^9$, $R^{10}$, $R^{11}$ are each independently hydrogen, $C_1$-$C_6$-alkyl, $C_1$-$C_6$-haloalkyl, $C_1$-$C_6$-alkylamino, $C_1$-$C_6$-alkoxy or $C_3$-$C_6$-cycloalkyl, wherein the carbon atoms of the last 5 groups may carry any combination of 1, 2 or 3 radicals, independently of one another selected from the group consisting of cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

$R^a$, $R^b$, $R^c$, $R^d$, $R^e$, $R^f$ are, independently of one another, hydrogen, $C_1$-$C_6$-alkyl, $C_1$-$C_6$-haloalkyl, $C_2$-$C_6$-alkenyl or $C_2$-$C_6$-alkynyl;

and the agriculturally acceptable salts thereof.

2. The compounds as claimed in claim 1, wherein $R^3$ is hydrogen or $C_1$-$C_4$-alkyl.

3. The compounds of claim 1, wherein $R^4$ is hydrogen, $C_1$-$C_4$-alkyl, $C_1$-$C_4$-haloalkyl, $C_1$-$C_4$-alkoxy-$C_1$-$C_4$-alkyl or phenyl, which is unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals.

4. The compounds of claim 1, wherein both $R^3$ and $R^4$ are hydrogen.

5. The compounds of claim 1, wherein $R^3$ is hydrogen and $R^4$ is selected from $C_1$-$C_4$-alkyl, $C_1$-$C_4$-haloalkyl, $C_1$-$C_4$-alkoxy-$C_1$-$C_4$-alkyl or phenyl, which is unsubstituted or substituted with 1 to 5 radicals, independently of one another selected from the group consisting of 5 halogen radicals, 3 $C_1$-$C_6$-alkyl, 3 $C_1$-$C_6$-haloalkyl, 3 $C_1$-$C_6$-alkylthio, 3 $C_1$-$C_6$-haloalkylthio, 3 $C_1$-$C_6$-alkoxy and 3 $C_1$-$C_6$-haloalkoxy radicals.

6. The compounds of claim 1, wherein A in formula I is a radical $A^1$, wherein $R^6$ is hydrogen, cyano, formyl, ($C_1$-$C_6$-alkyl)carbonyl, ($C_1$-$C_4$-haloalkyl)carbonyl, ($C_1$-$C_6$-alkoxy)carbonyl, ($C_1$-$C_6$-alkylthio)carbonyl or ($C_1$-$C_6$-alkoxy)methylen.

7. The compounds of claim 1, wherein A in formula I is a radical $A^2$, wherein $R^7$ is hydrogen.

8. The compounds of claim 1, wherein the radicals $R^8$, $R^9$, $R^{10}$ and $R^{11}$ are each hydrogen.

9. The compounds of claim 1, wherein at least one of the radicals $R^8$, $R^9$, $R^{10}$ and $R^{11}$ is different from hydrogen.

10. The compounds of claim 1, wherein n in formula I is 1, 2 or 3.

11. The compounds claim 1, wherein m in formula I is 1, 2 or 3.

12. The compounds of claim 10, wherein n+m is an integer from 1 to 6.

13. The compounds of claim 11, wherein n+m is an integer from 1 to 6.

14. The compounds of claim 1, wherein $R^5$ is hydrogen, cyano, formyl, $C_1$-$C_4$-alkyl, ($C_1$-$C_6$-alkyl)carbonyl, ($C_1$-$C_4$-haloalkyl)carbonyl, ($C_1$-$C_6$-alkoxy)carbonyl, ($C_1$-$C_6$-alkylthio)carbonyl or ($C_1$-$C_6$-alkoxy)methylen.

15. A method of combating animal pests, which comprises contacting said animal pests, their habit, breeding ground, food supply, plant, seed, soil, area, material or environment in which the animal pests are growing or may grow, or the materials, plants, seeds, soils, surfaces or spaces to be protected from attack or infestation by insects, arachnids or nematodes with a pesticidally effective amount of at least one compound of claim 1 and/or the agriculturally acceptable salts thereof.

16. The method as claimed in claim 15, wherein the pests are insects, arachnids or nematodes.

17. A method for protecting crops from attack or infestation by animal pests, which comprises contacting a crop with a pesticidally effective amount of at least one compound of claim 1 and/or the agriculturally acceptable salts thereof.

18. The method as claimed in claim 17, wherein the pests are insects, arachnids or nematodes.

19. A method for protecting non-living materials from attack or infestation by animal pests, the method comprising contacting the non-living material with a pesticidally effective amount of at least one compound of claim 1 and/or the agriculturally acceptable salts thereof.

20. The method of claim 19, wherein the pests are insects, arachnids or nematodes.

21. An agricultural composition comprising such an amount of at least one compound of claim 1 and/or the agriculturally acceptable salts thereof, that it exhibits a pesticidal action, and at least one inert solid and/or liquid carrier, and, optionally, at least one surfactant.

* * * * *

UNITED STATES PATENT AND TRADEMARK OFFICE
CERTIFICATE OF CORRECTION

| | | |
|---|---|---|
| PATENT NO. | : 7,871,960 B2 | Page 1 of 1 |
| APPLICATION NO. | : 11/914992 | |
| DATED | : January 18, 2011 | |
| INVENTOR(S) | : Markus Kordes et al. | |

It is certified that error appears in the above-identified patent and that said Letters Patent is hereby corrected as shown below:

Col. 33, line 7, delete "$C_1$-$C_o$" and insert therefore --$C_1$-$C_6$--; and

Col. 33, line 43, after "formyl," insert --$C_1$-$C_4$ alkyl,--

Signed and Sealed this
Fourteenth Day of June, 2011

David J. Kappos
*Director of the United States Patent and Trademark Office*